United States Patent [19]

Wetzel

[11] Patent Number: 4,885,107
[45] Date of Patent: Dec. 5, 1989

[54] SHAMPOO COMPOSITIONS

[75] Inventor: Thomas A. Wetzel, Cincinnati, Ohio

[73] Assignee: The Procter & Gamble Company, Cincinnati, Ohio

[21] Appl. No.: 178,715

[22] Filed: Apr. 7, 1988

Related U.S. Application Data

[63] Continuation-in-part of Ser. No. 47,823, May 8, 1987, abandoned.

[51] Int. Cl.$^4$ .............................................. C17D 3/60
[52] U.S. Cl. .................................... 252/106; 252/547; 252/548; 252/550; 252/551; 252/DIG. 13
[58] Field of Search ............... 252/547, 548, 550, 551, 252/106, DIG. 13

[56] References Cited

U.S. PATENT DOCUMENTS

| 2,694,669 | 11/1954 | Baldwin et al. | 167/87 |
| 3,152,046 | 10/1984 | Kapral | 167/87 |
| 3,970,584 | 7/1976 | Hart | 252/305 |
| 4,089,945 | 5/1978 | Brinkman | 424/164 |
| 4,470,981 | 9/1984 | Winkler | 424/245 |

FOREIGN PATENT DOCUMENTS

| 605826 | 9/1960 | Canada . |
| 0200305 | 2/1986 | European Pat. Off. . |
| 60810 | 5/1977 | Japan . |
| 1051268 | 3/1964 | United Kingdom . |
| 2170216 | 7/1986 | United Kingdom . |

OTHER PUBLICATIONS

Davidsohn et al., *Soap Manufacture*, vol. I, pp. 206, 210 (1953).
Grant et al., Grant & Hackh's Chemical Dictionary (5th Ed.) p. 360 (1987).

*Primary Examiner*—John F. Niebling
*Assistant Examiner*—Isabelle Rodriquez
*Attorney, Agent, or Firm*—Douglas C. Mohl; Steven J. Goldstein; Richard C. Witte

[57] ABSTRACT

Shampoos are disclosed which comprise a synthetic surfactant, selenium sulfide a suspending agent and water.

10 Claims, No Drawings

SHAMPOO COMPOSITIONS

CROSS REFERENCE TO RELATED APPLICATION

This is a continuation-in-part application of my copending application Ser. No. 047,823, filed May 8, 1987, now abandoned.

TECHNICAL FIELD

The present invention is related to antidandruff shampoos containing selenium sulfide, which shampoos are stabilized through the use of low levels of certain long chain materials or xanthan gum.

BACKGROUND OF THE INVENTION

Lotion shampoos are widely accepted due to their ease of use, including spreading the shampoo through the hair. However, when particulate active ingredients are used in lotion shampoos suspending active ingredients presents problems of various degrees. Suspension is desired so that the active concentration is the same, or close to the same, over several uses.

The prior art has recognized the need/desire for adequate suspension systems. Japanese Application with Open for Public Inspection No. 60,810, May 19, 1977 (Lion Fat & Oil), discloses shampoos containing 5% to 50% of an anionic surfactant, 1% to 10% of a fatty acid diethanol amide, 0.1% to 10% of an insoluble fine powder and 1% to 10% of an ethylene glycol ester. U.S. Pat. No. 4,470,982, to Winkler discloses similar compositions containing from 11% to 20% of an anionic surfactant, from 4% to 6% of a suspending agent, from 2% to 4% of an amide, a particulate antidandruff agent and water. British Pat. No. 1,051,268, Dec. 14, 1966 to Colgate-Palmolive Company discloses selenium sulfide shampoos containing suspending agents.

While these references disclose suspending antidandruff actives, they do not disclose compositions containing selenium sulfide and low levels of suspending agents.

It has been surprisingly found by the present inventors that certain selenium sulfide compositions can utilize low levels of suspending agents.

It is an object of the present invention, therefore, to provide stable selenium sulfide lotion shampoos.

It is a further object of the present invention to provide selenium sulfide lotion shampoos utilizing low levels of suspending agents.

It is a still further object of the present invention to provide methods of shampooing hair with improved selenium sulfide compositions.

These and other objects will become readily apparent from the detailed description which follows.

Unless otherwise indicated, all percentages and ratios herein are by weight.

SUMMARY OF THE INVENTION

The present invention relates to shampoo compositions comprising from about 10% to about 30% of a synthetic surfactant, from about 0.5% to about 3.5% of certain long chain derivatives or xanthan gum, from about 0.2% to about 2.5% of particulate selenium sulfide, from about 1% to about 10% of an alkanol amide and water. These as well as optional components are described in detail below.

DETAILED DESCRIPTION

The essential components of the present invention as well as optional components are given in the following paragraphs.

Surfactant

An essential component of the present compositions is a surfactant. The surfactant, which may be selected from any of a wide variety of synthetic anionic, amphoteric, zwitterionic and nonionic surfactants, is present at a level of from about 10% to about 30%, preferably from about 15% to about 22%, most preferably from about 18% to about 20%.

Synthetic anionic surfactants can be exemplified by the alkali metal salts of organic sulfuric reaction products having in their molecular structure an alkyl radical containing from 8-22 carbon atoms and a sulfonic acid or sulfuric acid ester radical (included in the term alkyl is the alkyl portion of higher acyl radicals). Preferred are the sodium, ammonium, potassium or triethanolamine alkyl sulfates, especially those obtained by sulfating the higher alcohols ($C_8$-$C_{18}$ carbon atoms), sodium coconut oil fatty acid monoglyceride sulfates and sulfonates; sodium or potassium salts of sulfuric acid esters of the reaction product of 1 mole of a higher fatty alcohol (e.g., tallow or coconut oil alcohols) and 1 to 12 moles of ethylene oxide; sodium or potassium salts of alkyl phenol ethylene oxide ether sulfate with 1 to 10 units of ethylene oxide per molecule and in which the alkyl radicals contain from 8 to 12 carbon atoms, sodium alkyl glyceryl ether sulfonates; the reaction product of fatty acids having from 10 to 22 carbon atoms esterified with isethionic acid and neutralized with sodium hydroxide; water soluble salts of condensation products of fatty acids with sarcosine; and other known in the art.

Zwitterionic surfactants can be exemplified by those which can be broadly described as derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate, or phosphonate. A general formula for these compounds is:

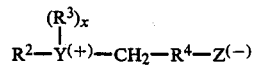

wherein $R^2$ contains an alkyl, alkenyl, or hydroxy alkyl radical of from about 8 to about 18 carbon atoms, from 0 to about 10 ethylene oxide moieties and from 0 to 1 glyceryl moiety; Y is selected from the group consisting of nitrogen, phosphorus, and sulfur atoms; $R^3$ is an alkyl or monohydroxyalkyl group containing 1 to about 3 carbon atoms; X is 1 when Y is a sulfur atom and 2 when Y is a nitrogen or phosphorus atom; $R^4$ is an alkylene or hydroxyalkylene of from 1 to about 4 carbon atoms and Z is a radical selected from the group consisting of carboxylate, sulfonate, sulfate, phosphonate, and phosphate groups.

Examples include:
4-[N,N-di(2-hydroxyethyl)-N-octadecylammonio]-butane-1-carboxylate;
5-[S-3-hydroxypropyl-S-hexadecylsulonio]-3-hydroxypentane-1-sulfate;

3-[P,P-diethyl-P-3,6,9-trioxatetradexocylphosphonio]-2-hydroxy-propane-1-phosphate;
3-[N-N-dipropyl-N-3-dodecoxy-2-hydroxypropylammonio]-propane-1-phosphonate;
3-(N,N-dimethyl-N-hexadecylammonio)propane-1-sulfonate;
3-(N,N-dimethyl-N-hexadecylammonio)-2-hydroxypropane-1-sulfonate;
4-[N,N-di(2-hydroxyethyl)-N-(2-hydroxydodecyl)ammonio]-butane-1-carboxylate;
3-[S-ethyl-S-(3-dodecoxy-2-hydroxypropyl)sulfonio]-propane-1-phosphate;
3-[P,P-dimethyl-P-dodecylphosphonio]-propane-1-phosphonate;
and
5-[N,N-di(3-hydroxypropyl)-N-hexadecylammonio]-2-hydroxy-pentane-1-sulfate.

Other zwitterionics such as betaines are also useful in the present invention. Examples of betaines useful herein include the high alkyl betaines such as coco dimethyl carboxymethyl betaine, lauryl dimethyl carboxymethyl betaine, lauryl dimethyl alpha-carboxyethyl betaine, cetyl dimethyl carboxymethyl betaine, lauryl bis-(2-hydroxy-ethyl) carboxy methyl betaine, stearyl bis-(2-hydroxy-propyl) carboxymethyl betaine, oleyl dimethyl gamma-carboxypropyl betaine, lauryl bis-(2-hyrdroxypropyl) alpha-carboxyethyl betaine, etc. The sulfobetaines may be represented by coco dimethyl sulfopropyl betaine, stearyl dimethyl sulfopropyl betaine, lauryl diemethyl sulfoethyl betaine, lauryl bis-(2-hyroxy-ethyl) sulfopropyl betaine and the like; amido betaines and amidosulfobetaines, wherein the RCONH(CH$_2$)$_3$ radical is attached to the nitrogen atom of the betaine are also useful in this invention.

Examples of amphoteric surfactants which can be used in the compositions of the present invention are those which can be broadly described as derivatives of aliphatic secondary and tertiary amines in which the aliphatic radical can be straight chain or branched and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products sold under the trade name "Miranol" and described in U.S. Pat. No. 2,528,378.

Nonionic surfactants, which are preferably used in combination with an anionic, amphoteric or zwitterionic surfactant, can be broadly defined as compounds produced by the condensation of alkylene oxide groups (hydrophilic in nature) with an organic hydrophobic compound, which may be aliphatic or alkyl aromatic in nature. Examples of preferred classes of nonionic surfactants are:

1. The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 60 moles of ethylene oxide per mole of alkyl phenol. The alkyl substituent in such compounds may be derived from polymerized propylene, diisobutylene, octane, or nonane, for example.

2. Those derived from the condensation of ethylene oxide with the product resulting from the reaction of propylene oxide and ethylene diamine products which may be varied in composition depending upon the balance between the hydrophobic and hydrophilic elements which is desired. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said base having a molecular weight of the order of 2,500 to 3,000, are satisfactory.

3. The condensation product of aliphatic alcohols having from 8 to 18 carbon atoms, in either straight chain or branched chain configuration, with ethylene oxide, e.g., a coconut alcohol ethylene oxide condensate having from 10 to 30 moles of ethylene oxide per mole of coconut alcohol, the coconut alcohol fraction having from 10 to 14 carbon atoms.

4. Long chains tertiary amine oxides corresponding to the following general formula:

$$R_1R_2R_3N \rightarrow O$$

wherein R$_1$ contains an alkyl, alkenyl or monohydroxy alkyl radical of from about 8 to about 18 carbon atoms, from 0 to about 10 ethylene oxide moieties, and from 0 to 1 glyceryl moiety, and R$_2$ and R$_3$ contain from 1 to about 3 carbon atoms and from 0 to about 1 hydroxy group, e.g., methyl, ethyl, propyl, hydroxy ethyl, or hydroxy propyl radicals. The arrow in the formula is a conventional representation of a semipolar bond. Examples of amine oxides suitable for use in this invention include dimethyl-dodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dode-coxyethyldimethylamine oxide, 3-dodecoxy-2-hydroxypropyldi(3-hydroxypropyl) amine oxide, dimethylhexadecylamine oxide.

5. Long chain tertiary phosphine oxides corresponding to the following general formula:

$$RR'R''P \rightarrow O$$

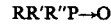

wherein R contains an alkyl, alkenyl or monohydroxyalkyl radical ranging from 8 to 18 carbon atoms in chain length, from 0 to about 10 ethylene oxide moieties and from 0 to 1 glyceryl moiety and R' and R" are each alkyl or monohydroxyalkyl groups containing from 1 to 3 carbon atoms. The arrow in the formula is a conventional representation of a semipolar bond. Examples of suitable phosphine oxides are: dodecyldimethylphosphine oxide, tetradecyldimethylphosphine oxide, tetradecylmethylethylphosphine oxide, 3,6,9,-trioxaoctadecyldimethylphosphine oxide, cetyldimethylphosphine oxide, 3-dodecoxy-2-hydroxypropyldi(2-hydroxyethyl)phosphine oxide, steartldimethylphosphine oxide, cetylethylpropylphosphine oxide, oleyldiethylphosphine oxide, dodecyldiethylphosphine oxide, tetradecyldiethylphosphine oxide, dodecyldipropylphosphine oxide, dodecyldi(hydroxymethyl)-phosphine oxide, dodecyldi(2-hydroxyethyl)phosphine oxide, tetradecylmethyl-2-hydroxypropylphosphine oxide, oleyldimethylphosphine oxide, 2-hydroxyldodecyldimethylphosphine oxide.

6. Long chains dialkyl sulfoxides containing one short chain alkyl or hydroxy alkyl radical of 1 to about 3 carbon atoms (usually methyl) and one long hydrophobic chain which contain alkyl, alkenyl, hydroxy alkyl, or keto alkyl radicals containing from about 8 to about 20 carbon atoms, from 0 to about 10 ethylene oxide moieties and from 0 to 1 glyceryl moiety. Examples include: octadecyl methyl sulfoxide, 2-ketotridecyl methyl sulfoxide, 3,6,9,-trioxaoctadecyl 2-hydroxyethyl suffoxide, dodecyl methyl sulfoxide, oleyl 3-hydroxypropyl sulfoxide, tetradecyl methyl sulfoxide, 3-methoxytridecyl methyl sulfoxide, 3-hydroxy-tridecyl methyl sulfoxide, 3-hydroxy-4-dodecoxybuty methyl sulfoxide.

Many additional nonsoap surfactants are described in McCUTCHEON'S, DETERGENTS AND EMULSIFIERS, 1986 ANNUAL, published by Allured Publishing Corporation, which is incorporated herein by reference.

The above-mentioned surfactants can be used alone or in combination in the shampoo compositions of the present invention. The anionc surfactants, particularly the alkyl sulfates, the ethoxylated alkyl sulfates and mixtures thereof are preferred for use herein as well as the isethionates.

Long Chain Derivative or Xanthan Gum Suspending Agent

The suspending agent useful in the present compositions can, for example, be any of several long chain acyl derivative materials or mixtures of such materials. Included are ethylene glycol diesters wherein the esters are a mixture of palmitate and stearate. The amount of sterate should be in the range of about 10% to about 42% or in the range of about 55% to about 80%, preferably from about 60% to about 75%, with palmitate accounting for the remainder. Still other suspending agents found useful are alkanol amides of fatty acids, having from about 16 to about 22 carbon atoms, preferably about 16 to 18 carbon atoms. Preferred alkanol amides are stearic monoethanolamide, stearic diethanolamide and stearic monoisopropanolamide. Still other long chain acyl derivatives include long chain esters of long chain fatty acids (e.g., stearyl stearate, cetyl palmitate, etc.); glyceryl esters (e.g., glyceryl distearate) and long chain esters of long chain alkanol amides (e.g., stearamide DEA distearate, stearamide MEA stearate).

Still other suitable suspending agents are alkyl ($C_{16-22}$) dimethyl amine oxides such as stearyl dimethyl amine oxide. If the compositions contain an amine oxide or a long chain acyl derivative as a surfactant the suspending function could also be provided and additional suspending agent may not be needed if the level of those materials are at least the minimum level given below.

Xanthan gum is another agent used to suspend the selenium sulfide in the present compositions. This biosynthetic gum material is commercially available and is a heteropolysaccharide with a molecular weight of greater than 1 million. It is believed to contain D-glucose, D-mannose and D-glucuronate in the molar ratio of 2.8:2.0:2.0. The polysacchardie is partially acetylated with 4.7% acetyl. This information and other is found in Whistler, Roy L. Editor *Industrial Gums—Polysaccharides and Their Derivatives* New York: Academic Press, 1973. Kelco, a Division of Merck & Co., Inc. offers xanthan gum as Keltrol ®.

The suspending agent is present at a level of from about 0.50% to about 5.0%, preferably from about 0.5% to about 3.0%. The suspending agent serves to assist in suspending the selenium sulfide and may give pearlescence to the product. Mixtures of suspending agents are also suitable for use in the compositions of this invention.

Selenium Sulfide

Selenium sulfide is a staple item of commerce. While selenium sulfide as provided by suppliers can be used in the present compositions, it is preferred to agglomerate the material to create larger particles. This is accomplished by dispersing the powdered selenium sulfide into a water/surfactant mixture wherein the material is agglomerated into particles in the 10 to 50 micron range, with an average of about 25 microns. These measurements are made using a forward laser light scattering device (e.g., a Malvern 3600 instrument).

Selemium sulfide is present in the compositions of this invention at a level of from about 0.2% to about 2.5%, preferably from about 0.9% to about 1.5%.

Alkanol Amide

The amide used in the present compositions can be any of the alkanolamides of fatty acids known for use in shampoos. These are generally mono- and diethanolamides of fatty acids having from about 8 to 14 carbon atoms. Preferred are coconut monoethanolamide, lauric diethanolamide and mixtures thereof.

The amide is present at a level of from about 1% to about 10%.

Water

Water is the last essential component of the present invention and forms the remainder of the composition. It is generally present at a level of from about 20% to about 95%, preferably from about 60% to about 85%.

Optional Components

The shampoos herein can contain a variety of nonessential optional components suitable for rendering such compositions more acceptable. Such conventional optional ingredients are well known to those skilled in the art, e.g., preservatives such as benzyl alcohol, methyl paraben, propyl paraben and imidazolidinyl urea; silicone oils and gums such as methylsiloxanes; cationic surfactants such as cetyl trimethyl ammonium chloride, lauryl trimethyl ammonium chloride, tricetyl methyl ammonium chloride, stearyldimethyl benzyl ammonium chloride, and di(partially hydrogenated tallow) dimethylammonium chloride; menthol; thickeners and viscosity modifiers such as block polymers of ethylene oxide and propylene oxide such as Pluronic F88 offered by BASF Wyandotte, sodium chloride, sodium sulfate, polyvinyl alcohol, propylene glycol, and ethyl alcohol; pH adjusting agents such as citric acid, succinic acid, phosphoric acid, sodium hydroxide, sodium carbonate, etc.; perfumes; dyes; and, sequestering agents such as disodium ethylenediamine tetraacetate. Such agents generally are used individually at a level of from about 0.01% to about 10%, preferably from about 0.5% to about 5.0% by weight of the composition.

METHOD OF MANUFACTURE

One method for manufacturing the present composition is described below.

All ingredients except the selenium sulfide are mixed together and heated to about 72° C. The mixture is mixed thoroughly for about 10 minutes at 72° C. before pumping through a high shear mill and then through a heat exchanger to cool to about 27° C. The selenium sulfide is then added at 27° C. and it is thoroughly mixed.

In the cooling step, the acyl derivative is preferably crystallized into particles having an average particle size of about 10μ or less.

In an alternative process a part of the surfactant is not added until after the product has cooled. This may help control the crystallization of the acyl derivative.

INDUSTRIAL APPLICABILITY

The present compositions are used in a conventional manner for cleaning hair. From about 0.1 g to about 10 g of a composition is applied to hair that has been wetted, generally with water, worked through the hair and then rinsed out.

The following Examples further describe and demonstrate the preferred embodiments within the scope of the present invention. The Examples are given solely for the purpose of illustration and are not to be construed as limitations of the present invention as many variations thereof are possible without departing from its spirit and scope.

EXAMPLES I-IV

The following compositions are representative of the present invention.

| Component | I | II | III | IV |
|---|---|---|---|---|
| Ammonium lauryl sulfate (25%) | 38.000 | 38.000 | 60.000 | 30.000 |
| Ammonium AE$_3$S (27.5%) | 37.200 | 37.200 | 0.000 | 30.000 |
| Ammonium xylene sulfonate | 5.000 | 5.000 | 3.000 | 3.000 |
| Cocamide MEA | 4.000 | 4.000 | 3.000 | 5.000 |
| Propylene glycol | 0.000 | 0.750 | 0.000 | 1.000 |
| Glycol distearate | 3.000 | 3.000 | 2.500 | 3.000 |
| Preservative | 0.033 | 0.033 | 0.033 | 0.033 |
| Perfume | 0.650 | 0.650 | 0.500 | 0.500 |
| Citric acid | 0.150 | 0.150 | 0.150 | 0.150 |
| Selenium sulfide (25%) | 4.000 | 4.000 | 4.000 | 4.000 |
| Menthol | 0.500 | 0.500 | 0.000 | 0.350 |
| Double reverse osmosis water | Balance | | | |
| TOTALS | 100.000 | 100.000 | 100.000 | 100.000 |

What is claimed is:

1. A shelf stable shampoo composition consisting essentially of:
   (a) from about 10% to about 25% of a synthetic surfactant;
   (b) from about 0.5% to about 3.0% of ethylene glycol long chain ($C_{16}$–$C_{22}$) diesters having a stearate to palmitate ratio of about 10% to about 42% stearate to about 90% to about 58% palmitate and about 55% to about 80% stearate to about 45% to about 20% palmitate;
   (c) from about 0.2% to about 2.5% of selenium sulfide;
   (d) from about 1% to about 10% of an alkanol amide of fatty acid having from about 8 to about 14 carbon atoms; and
   (e) the remainder water.

2. A shampoo composition according to claim 1 wherein the surfactnat is selected from the group consisting of anionic surfactants, zwitterionic surfactants, amphoteric surfactants and mixtures thereof.

3. A shampoo composition according to claim 2 wherein the surfactant is anionic.

4. A shampoo composition according to claim 3 wherein the anionic surfactant is a mixture of alkyl sulfate and ethoxylated alkyl sulfate surfactants.

5. A shampoo composition according to claim 4 which in addition contains menthol.

6. A shampoo composition according to claim 5 wherein the selenium sulfide is present at a level of from about 0.9% to about 1.5%.

7. A method of shampooing hair comprising applying to hair that has been wet with water from about 0.10 g to about 10 g of a composition according to claim 1, working the composition through the hair and rinsing it from the hair.

8. A method of shampooing hair comprising applying to hair that has been wet with water, from about 0.10 g to about 10 g of a composition according to claim 3.

9. A method of shampooing hair comprising applying to hair that has been wet with water, from about 0.10 g to about 10 g of a composition according to claim 5.

10. A method of shampooing hair comprising applying to hair that has been wet with water, from about 0.10g to about 10g of a composition according to claim 6.

* * * * *

UNITED STATES PATENT AND TRADEMARK OFFICE
CERTIFICATE OF CORRECTION

PATENT NO. : 4,885,107

DATED : December 5, 1989

INVENTOR(S) : Thomas A. Wetzel

It is certified that error appears in the above-identified patent and that said Letters Patent is hereby corrected as shown below:

Column 6 at line 65 the following paragraph should be inserted:

-- The pH of the present compositions is not critical and may be in the range of from 2 to about 10, preferably from about 4 to about 7. --

Signed and Sealed this

Second Day of July, 1991

Attest:

HARRY F. MANBECK, JR.

Attesting Officer

Commissioner of Patents and Trademarks